(12) United States Patent
Nappa et al.

(10) Patent No.: US 7,343,981 B2
(45) Date of Patent: Mar. 18, 2008

(54) METHODS USING FLUOROKETONES FOR: EXTINGUISHING FIRE; PREVENTING FIRE, AND REDUCING OR ELIMINATING THE FLAMMABILITY OF A FLAMMABLE WORKING FLUID

(75) Inventors: Mario J. Nappa, Newark, DE (US); Velliyur Nott Mallikarjuna Rao, Wilmington, DE (US); Allen C. Sievert, Elkton, MD (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 457 days.

(21) Appl. No.: 10/871,715

(22) Filed: Jun. 18, 2004

(65) Prior Publication Data

US 2005/0023007 A1 Feb. 3, 2005

Related U.S. Application Data

(60) Provisional application No. 60/479,559, filed on Jun. 18, 2003.

(51) Int. Cl.
*A62C 2/00* (2006.01)

(52) U.S. Cl. .............................. 169/46; 169/9; 169/11; 169/44; 252/2; 252/8; 568/416

(58) Field of Classification Search .................. 169/43, 169/44, 45, 46, 9, 11; 252/2, 8; 568/416, 568/419
See application file for complete search history.

(56) References Cited

U.S. PATENT DOCUMENTS 4,420,638 A * 12/1983 Uschold .................... 568/416
5,718,293 A * 2/1998 Flynn et al. ................. 169/45
5,900,185 A    5/1999 Tapscott
5,919,393 A * 7/1999 Flynn et al. ................. 252/2
6,031,011 A    2/2000 Tapscott
6,300,378 B1  10/2001 Tapscott
6,478,979 B1  11/2002 Rivers et al.
6,630,075 B2 * 10/2003 Behr et al. ................. 568/419
7,122,704 B2 * 10/2006 Nappa et al. ................. 252/2

OTHER PUBLICATIONS

Zapevalov, A. Ya. et al., "Synthesis and Reactions of Oxygen-Containing Organofluorine Compouds. X. Bromoperfluorinated Carbonyl Compounds and Their Derivatives", Database Caplus Online Search, Chemical Abstracts Service, Abstract cited (Zhurnal Organicheskoi Khimii), 1990, pp. 265-272, vol. 26(2)., Inst. Khim., Sverdlovsk, USSR.
International Search Report.

* cited by examiner

Primary Examiner—Steven J. Ganey

(57) ABSTRACT

The present invention relates to methods of using at least one fluoroketone selected from monobromoperfluoroketones, monohydromonobromoperfluoroketones, (perfluoroalkoxy) monobromoperfluoroketones, (fluoroalkoxy)monobromoperfluoroketones, and monochloromonobromoperfluoroketones for i) extinguishing fire by applying to the fire such a fluoroketone, ii) preventing fire in an air-containing enclosed area containing combustible materials by introducing into the area such a fluoroketone and maintaining the fluoroketone in an amount sufficient to suppress combustion of combustible materials in the enclosed area, and iii) reducing or eliminating the flammability of a flammable working fluid, by mixing between about 0.1 to about 99 percent by weight of such a fluoroketone with the flammable working fluid.

14 Claims, No Drawings

METHODS USING FLUOROKETONES FOR: EXTINGUISHING FIRE; PREVENTING FIRE, AND REDUCING OR ELIMINATING THE FLAMMABILITY OF A FLAMMABLE WORKING FLUID

CROSS REFERENCE(S) TO RELATED APPLICATION(S)

This application claims the priority benefit of U.S. Provisional Application 60/479,559, filed Jun. 18, 2003

BACKGROUND OF THE INVENTION

1. Field of the Invention

The present invention relates to methods for extinguishing fire, preventing fire, and reducing or eliminating the flammability of a flammable working fluid using monobromoperfluoroketones, monohydromonobromoperfluoroketones, (perfluoroalkoxy)monobromoperfluoroketones, (fluoroalkoxy)monobromoperfluoroketones, and monochloromonobromoperfluoroketones.

2. Description of Related Art

Numerous agents and methods of fire fighting are known and can be selected for a particular fire, depending upon factors such as its size, location and the type of combustible materials involved. Halogenated hydrocarbon fire fighting agents have traditionally been utilized in flooding applications protecting fixed enclosures (e.g., computer rooms, storage vaults, telecommunications switching gear rooms, libraries, document archives, petroleum pipeline pumping stations, and the like), or in streaming applications requiring rapid extinguishing (e.g., military aircraft, commercial hand-held extinguishers). Such extinguishing agents are not only effective but, unlike water, also function as "clean extinguishing agents," causing little, if any, damage to the enclosure or its contents.

The most commonly-used halogenated hydrocarbon extinguishing agents have been the bromine-containing compounds bromotrifluoromethane ($CF_3Br$, Halon™1301) and bromochlorodifluoromethane ($CF_2ClBr$, Halon™1211). These bromine-containing halocarbons are highly effective in extinguishing fires and can be dispensed either from portable streaming equipment or from an automatic room flooding system activated either manually or by some method of fire detection. However, these compounds have been linked to ozone depletion. The Montreal Protocol and its attendant amendments have mandated that Halon™1211 and 1301 production be discontinued.

Thus, there is a need in this field for methods using substitutes or replacements for the commonly-used, bromine-containing fire extinguishing agents. Such substitutes used in such methods should have a low ozone depletion potential; should have the ability to extinguish, control, and prevent fires, e.g., Class A (trash, wood, or paper), Class B (flammable liquids or greases), and/or Class C (electrical equipment) fires; and should be "clean extinguishing agents," i.e., be electrically non-conducting, volatile or gaseous, and leave no residue upon use. Preferably, such substitutes used in such methods will also be low in toxicity, not form flammable mixtures in air, have acceptable thermal and chemical stability for use in extinguishing applications, and have short atmospheric lifetimes and low global warming potentials.

Various different fluorinated hydrocarbons have been suggested for use as fire fighting agents. For example, in U.S. Pat. No. 6,300,378, Tapscott discloses tropodegradeable bromine-containing halocarbon additives to decrease the flammability of refrigerants, foam blowing agents, solvents, aerosol propellants, and sterilants. In U.S. Pat. No. 6,478,979, Rivers et al. disclose the use of perfluorinated ketones in fire extinguishing.

BRIEF SUMMARY OF THE INVENTION

The aforementioned objectives of methods using substitutes or replacements for the commonly-used, bromine-containing fire extinguishing agents are met by the present invention which comprises methods for extinguishing fire, preventing fire, and reducing or eliminating the flammability of a flammable working fluid using monobromoperfluoroketones, monohydromonobromoperfluoroketones, (perfluoroalkoxy)monobromoperfluoroketones, (fluoroalkoxy)monobromoperfluoroketones, and monochloromonobromoperfluoroketones.

DETAILED DESCRIPTION OF THE INVENTION

The term "fluoroketones" will be at points herein to refer collectively to the classes monobromoperfluoroketones, (perfluoroalkoxy)monobromoperfluoroketones, (fluoroalkoxy)monobromoperfluoroketones, monohydromonobromoperfluoroketones, and monochloromonobromoperfluoroketones, that may be used in the methods of the present invention.

The present fluoroketones may be utilized alone, in combination with one another, or in combination with a co-firefighting agent or propellant selected from known fire fighting agents of the classes hydrofluorocarbons, hydrochlorofluorocarbons, perfluorocarbons, perfluoroketones, perfluoropolyethers, hydrofluoropolyethers, hydrofluoroethers, chlorofluorocarbons, bromofluorocarbons, bromochlorofluorocarbons, hydrobromocarbons, iodofluorocarbons, and hydrobromofluorocarbons. Such co-agents can be chosen to enhance the fire fighting capabilities or modify the physical properties (e.g., modify the rate of introduction by serving as a propellant) of a fire fighting composition for a particular type (or size or location) of fire hazard and can preferably be utilized in ratios (of co-agent to fluoroketone) such that the resulting composition does not form flammable mixtures in air. Such fire fighting mixtures may contain from about 10-90% by weight of at least one fluoroketone and from about 90-10% by weight of at least one co-agent.

The present fluoroketones may be utilized additionally in combination with a propellant (e.g., for expelling a liquid fluoroketone from a sealed vessel), where the propellant is moderately flammable or flammable, provided that the resultant composition comprising fluoroketone and such propellant is non-flammable.

Of particular utility are azeotropic and azeotrope-like mixtures containing the present fluoroketones and one or more compounds selected from the group consisting of perfluoroketones and hydrofluorocarbons. Such mixtures may provide a fire fighting composition with a lower boiling point than either constituent of the mixture as well as provide a constant ratio of the components of the mixture during discharge.

The present fluoroketones may be solids, liquids, or gases under ambient conditions, but are preferably utilized for the present methods of fire preventing and extinguishing in either the liquid or the gaseous state (or both). Thus, normally solid compounds are preferably utilized after transformation to liquid and/or gas through melting, sublimation, or dissolution in a liquid co-agent. Such transformation can occur upon exposure of the compound to the heat of a fire.

The present invention includes a method of extinguishing a fire comprising applying to said fire a composition comprising at least one compound selected from the group consisting of monobromoperfluoroketones, monohydromonobromoperfluoroketones, (perfluoroalkoxy)monobromoperfluoroketones, (fluoroalkoxy)monobromoperfluoroketones, and monochloromonobromoperfluoroketones in an amount sufficient to extinguish said fire.

The extinguishing method of the present invention can be carried out by introducing the composition into an enclosed area surrounding a fire. Any of the known methods of introduction can be utilized provided that appropriate quantities of the composition are metered into the enclosed area at appropriate intervals. For example, a composition can be introduced by streaming, e.g., using conventional portable (or fixed) fire extinguishing equipment; by misting; or by flooding, e.g., by releasing (using appropriate piping, valves, and controls) the composition into an enclosed area surrounding a fire. The composition can optionally be combined with an inert propellant, e.g., nitrogen, argon, decomposition products of glycidyl azide polymers or carbon dioxide, to increase the rate of discharge of the composition from the streaming or flooding equipment utilized. When the composition is to be introduced by streaming or local application, fluoroketones having normal boiling points in the range of from about 40° C. to about 130° C. (especially fluoroketones that are liquid under ambient conditions) are preferably utilized. When the composition is to be introduced by misting, fluoroketones having boiling points in the range of from about 40° C. to about 110° C. are generally preferred. And, when the composition is to be introduced by flooding, fluoroketones having boiling points in the range of from about 40° C. to about 80° C. are generally preferred.

Preferably, the extinguishing process of the present invention involves introducing fluoroketone to a fire or flame in an amount sufficient to extinguish the fire or flame. One skilled in this field will recognize that the amount of fluoroketone needed to extinguish a particular fire will depend upon the nature and extent of the hazard. When the fluoroketone is to be introduced by flooding, cup burner test data is useful in determining the amount or concentration of fluoroketone required to extinguish a particular type and size of fire. The amount of fluoroketone used to extinguish fire is generally an average resulting concentration of between about 1 and about 10 percent by gas volume of fluoroketone.

The method the present invention further includes preventing fire in an air-containing enclosed area containing combustible materials comprising introducing into said area a composition comprising at least one compound selected from the group consisting of monobromoperfluoroketones, monohydromonobromoperfluoroketones, (perfluoroalkoxy) monobromoperfluoroketones, (fluoroalkoxy)monobromoperfluoroketones, and monochloromonobromoperfluoroketones, and maintaining said composition in an amount sufficient to suppress combustion of combustible materials in the enclosed area.

Thus, the present invention further includes a method of using fluoroketones for preventing a combustible material from igniting. The present method using fluoroketones may prevent fires or deflagration in an air-containing, enclosed area that contains combustible materials of the self-sustaining or non-self-sustaining type. This method comprises the step of introducing into an air-containing, enclosed area a non-flammable fire preventing composition that is essentially gaseous that comprises at least one present fluoroketone, the composition being introduced and maintained in an amount sufficient to prevent combustion of combustible materials in the enclosed area.

For fire prevention, fluoroketones (and any co-agent(s) utilized) can be chosen so as to provide a composition that is essentially gaseous under use conditions. Preferred fluoroketones for this method have normal boiling points in the range of from about 40° C. to about 130° C. The fluoroketone composition is introduced and maintained in an amount sufficient to prevent combustion of combustible materials in the enclosed area. The amount varies with the combustibility of the particular flammable materials present in the enclosed area. Combustibility varies according to chemical composition and according to physical properties such as surface area relative to volume, porosity, etc. The present fluoroketones can be used to eliminate the combustion-sustaining properties of air and to thereby prevent the combustion of flammable materials (e.g., paper, cloth, wood, flammable liquids, and plastic items). The present fluoroketones can be maintained continuously if a threat of fire is always present or can be introduced into an atmosphere as an emergency measure if a threat of fire or deflagration develops.

The present invention further includes a method of reducing or eliminating the flammability of a flammable working fluid, comprising: a) providing an additive comprising at least one compound selected from the group consisting of monobromoperfluoroketones, monohydromonobromoperfluoroketones, (perfluoroalkoxy)monobromoperfluoroketones, (fluoroalkoxy)monobromoperfluoroketones, and monochloromonobromoperfluoroketones, and b) mixing between about 0.1 to about 99 percent by weight of said additive with said flammable working fluid.

Flammable working fluids may comprise refrigerants (e.g., propane, propylene, difluoromethane (HFC-32), 1,1-difluoroethane (HFC-152a), 1,1,1-trifluoroethane (HFC-143a)), foam blowing agents (e.g., cyclopentane, n-pentane, iso-pentane, n-butane, iso-butane, dimethyl ether, 1,1-difluoroethane (HFC-152a), 1,1-dichloro-1-fluoroethane (HCFC-141b)), solvents (e.g., monochlorotoluenes, benzotrifluorides, volatile methyl siloxanes, terpenes, alcohols, petroleum distillates, hydrocarbons, ethers, esters, ketones), aerosol propellants (e.g., dimethyl ether, 1,1-difluoroethane (HFC-152a)), and/or sterilants (e.g., hydrocarbon epoxides (ethylene oxide)).

This further method of the present invention uses the aforementioned fluoroketones as additives to reduce or eliminate the flammability of normally flammable working fluids. The aforementioned fluoroketones have the characteristics of high effectiveness for flammability reduction, but have short atmospheric lifetimes (on the order of days or weeks) resulting in low ozone depletion potentials and global warming potentials.

The amount of fluoroketone needed will depend on the application, the material whose flammability is to be reduced, and the specific fluoroketone. The fluoroketones will be most useful at concentrations ranging from 1-80% by weight, although the concentration of fluoroketone in the mixtures can range from 0.1-99% by weight. Expedient proportions include 5-40% by weight of fluoroketone for refrigerant mixtures, 5-50% by weight of fluoroketone for foam blowing agent mixtures, 1-99% fluoroketone for solvent mixtures, 5-25% by weight fluoroketone for aerosol propellant mixtures, and 5-40% by weight fluoroketone for sterilant mixtures.

Refrigerants, foam blowing agents, solvents, aerosol propellants, and/or sterilants may be either gases (vapors) or liquids. In many cases, materials are stored in one form and used in another. For example, foam blowing agents may be stored as a liquid and used as a gas when the foam is actually blown. In some cases, both gaseous and liquid forms are present during use. Thus, refrigerants are present in both vapor and liquid forms during the operation of most refrigerators or heat pumps. In the gas phase, normally flammable refrigerants, foam blowing agents, solvents, aerosol propellants, and/or sterilants containing the flammability reducing fluoroketone will have a reduced flammability due to the presence of the fluoroketone. Of particular importance is the action of the fluoroketone when the refrigerant, foam blowing agent, solvent, aerosol propellant, and/or sterilant is in the liquid state. The present fluoroketones are volatile, though some are more-so and some less-so. Thus, normally flammable liquid refrigerants, foam blowing agents, solvents, aerosol propellants, and sterilants containing these fluoroketones will, upon full or partial evaporation, produce vapors that have lower flammabilities due to the presence of the flammability reducing fluoroketones, which also evaporate. Of particular importance is that release of the fluoroketones when refrigerants, foam blowing agents, solvents, aerosol propellants, and refrigerants evaporate or are otherwise released into an area will aid in reducing flammability of the vapor above the liquid/vapor interface (i.e., combustible liquids) and explosivity of the vapor if released into a volume such as a room.

Monobromoperfluoroketones comprise perfluorinated ketones containing one bromine substituent and may be generally represented by the formula $R^1C(O)R^2$, wherein $R^1$ is a $C_1$-$C_5$ perfluoroalkyl radical, and $R^2$ is a $C_1$-$C_5$ monobromoperfluoroalkyl radical. Monobromoperfluoroketones include the known monobromoperfluoroketones, for example: $CBrF_2C(O)CF_3$, $CBrF_2C(O)CF_2CF_3$, $CF_3C(O)CBrFCF_3$, $CF_3C(O)CF_2CBrF_2$, $CBrF_2C(O)CF_2CF_2CF_3$, $CF_3C(O)CBrFCF(CF_3)_2$, $CBrF_2C(O)CF(CF_3)CF_3$, $CBrF_2CF_2C(O)CF(CF_3)_2$, $CF_3CBrFC(O)CF(CF_3)_2$, $CF_3CF_2C(O)CBr(CF_3)_2$, and $CF_3CF_2C(O)CF(CBrF_2)(CF_3)$.

The new monobromoperfluoroketones $CF_3C(O)CF_2CF_2CBrF_2$, $CF_3CF_2C(O)CF_2CF_2CBrF_2$ and $CF_3C(O)CF_2CF_2CF_2CBrF_2$, useful in the method of the present invention, may be prepared by bromination of the corresponding monohydroperfluoroketones by the technique of Kolenko and Plashkin in *Izvestiya Akademii Nauk SSSR, Seriya Khimicheskaya*, pages 1648 to 1650 (1977), and by Zapevalov, et al. in *Zhurnal Organicheskoi Khimii*, Vol. 26, pages 265 to 272 (1990). $CF_3C(O)CF_2CF_2CBrF_2$ may be prepared by bromination of monohydroperfluoroketone $CF_3C(O)CF_2CF_2CHF_2$, which may be prepared by isomerization of an epoxide as described by Zapelov et al. in *Zhurnal Vsesoyuznogo Khimicheskogo Obshchestva im. D. I. Mendeleeva*, Vol. 18, pages 591 to 593 (1973). $CF_3CF_2C(O)CF_2CF_2CBrF_2$ and $CF_3C(O)CF_2CF_2CF_2CBrF_2$ may be prepared by bromination of monohydroperfluoroketones $CF_3CF_2C(O)CF_2CF_2CHF_2$ and $CF_3C(O)CF_2CF_2CF_2CF_2CHF_2$, respectively, by the technique of Saloutina, et al. in *Zhurnal Organicheskoi Khimii*, Vol. 29, pages 1325 to 1336 (1993).

Preparation of the new monobromoperfluoroketones $CF_3C(O)CF_2CF_2CBrF_2$, $CF_3CF_2C(O)CF_2CF_2CBrF_2$ and $CF_3C(O)CF_2CF_2CF_2CBrF_2$, useful in the method of the present invention, may be carried out by conversion of the monohydroperfluoroketone terminal C—H bond to a terminal C—Br may be carried out using brominating agents such as elemental bromine, phosphorous pentabromide, or a mixture of bromine and phosphorous tribromide. The preferred brominating agent is a mixture of bromine and phosphorous tribromide.

Reaction of a monohydroperfluoroketone and a brominating agent may be carried out under substantially anhydrous conditions in the vapor phase or liquid phase in a container fabricated from materials of construction suitable for contact with bromine and hydrogen bromide at temperatures of about 300° C. to 600° C. Examples of such materials of construction include metallic alloys containing a nickel such as, for example, Hastelloy™ C and Hastelloy™ B. The reaction takes place under the autogenous pressures of the reactants at the reaction temperature.

The ratio of the brominating agent to the monohydroperfluoroketones is at least about 1 mole of brominating agent per mole of monohydroperfluoroketone and preferably about 1.3 moles of brominating agent per mole of monohydroperfluoroketone. More than 1.7 moles of brominating agent per mole of monohydroperfluoroketone provides little benefit.

Brominating the monohydroperfluoroketone may be conducted at temperatures of from about 300° C. to about 600° C. Using the preferred brominating agent, the temperature is preferably conducted from about 300° C. to 350° C. Contact times between the brominating agent and the monohydroperfluoroketone may be from about one hour to about twenty hours.

At the end of the contact period the reaction mixture is cooled and then treated with a reagent to decompose the brominating agent such as sodium sulfite. The monobromoperfluoroketone may be isolated by collecting the organic phase followed by distillation.

The new monobromoperfluoroketones $CF_3CF_2C(O)CBrFCF_2CF_3$, $CF_3CF_2CBrFC(O)CF(CF_3)_2$, $(CF_3)_2CBrC(O)CF(CF_3)_2$, $CF_3CF_2C(O)CBr(CF_3)CF_2CF_3$ and $CF_3CBrFC(O)CF(CF_3)CF_2CF_3$, as well as mixtures of monobromoperfluoroketones $CF_3C(O)CBrFCF_2CF_3$ and $CF_3CBrFC(O)CF_2CF_3$, or $CF_3C(O)CBrFCF_2CF_2CF_3$ and $CF_3CBrFC(O)CF_2CF_2CF_3$, or $CF_3CF_2C(O)CBrFCF_2CF_3$ and $CF_3CF_2CBrFC(O)CF_2CF_2CF_3$, useful in the method of the present invention, may be prepared by reacting perfluoroolefin epoxides, such as the epoxide of perfluoro-2-pentene, perfluoro-2-heptene, or perfluoro-3-heptene, with an alkali metal bromide as described by Saloutina et al. in *Izvestiya Akademii Nauk SSSR, Seriya Khimicheskaya*, pages 1893 to 1896 (1982). The perfluoroolefin epoxides may be prepared by reaction of the perfluoroolefin with an alkali metal hypohalite as described by Kolenko, et al. in *Izvestiya Akademii Nauk SSSR, Seriya Khimicheskaya*, pages 2509-2512 (1979).

The reaction of perfluoroolefin epoxides with alkali metal bromides may be carried out in a polar non-protic solvent such as glycol ethers such as ethylene glycol dimethyl ether, diethylene glycol dimethyl ether, triethylene glycol dimethyl ether, and tetraethylene glycol dimethyl ether, N,N-dimethyl formamide, N,N-dimethyl acetamide, dimethyl sulfolane, dimethylsulfoxide, N-methylpyrrolidinone, and alkane nitriles such as acetonitrile, propionitrile, and butyronitrile. Preferred solvents for contacting perfluoroolefin epoxides with alkali metal bromides are glycol ethers such as ethylene glycol dimethyl ether, diethylene glycol dimethyl ether, triethylene glycol dimethyl ether, and tetraethylene glycol dimethyl ether, and alkane nitriles such as acetonitrile, propionitrile, and butyronitrile.

Alkali metal bromides suitable for opening the perfluoroolefin epoxide ring and formation of a C—Br bond include lithium bromide, sodium bromide, potassium bromide, and cesium bromide; sodium and lithium bromide are preferred.

The mole ratio of the alkali metal bromide to the perfluoroolefin epoxide is at least about 2:1, preferably about 10:1.

Reaction of alkali metal bromides and perfluoolefin epoxide may be conducted in the liquid phase under substantially anhydrous conditions at temperatures of from about 10° C. to about 150° C., with contact times of from about 0.5 hour to about thirty-six hours. The pressure under which the reaction occurs is not critical.

At the end of the contact period the reaction mixture may be distilled to isolate the monobromoperfluoroketone.

The new monobromoperfluoroketones $CBrF_2C(O)CF(CF_3)_2$, $CBrF_2CF_2C(O)CF_2CF_3$, $CF_3CF_2C(O)CF_2CF_2CF_2CBrF_2$, $CBrF_2CF_2CF_2C(O)CF(CF_3)_2$, $CBrF_2CF_2C(O)CF(CF_3)CF_2CF_3$ and $CF_3CBrFCF_2C(O)CF(CF_3)_2$, useful in the method of the present invention, may be prepared by reacting a monobromoperfluoroacyl fluoride with a perfluoroolefin.

$CBrF_2C(O)CF(CF_3)_2$ may be prepared by reacting $CBrF_2C(O)F$ with $CF_3CF=CF_2$; $CBrF_2CF_2C(O)CF_2CF_3$ may be prepared by reacting $CBrF_2CF_2C(O)F$ with $CF_2=CF_2$; $CF_3CF_2C(O)CF_2CF_2CF_2CBrF_2$ may be prepared by reacting $CBrF_2CF_2CF_2CF_2C(O)F$ with $CF_2=CF_2$; $CBrF_2CF_2CF_2C(O)CF(CF_3)_2$ may be prepared by reacting $CBrF_2CF_2CF_2C(O)F$ with $CF_3CF=CF_2$; $CBrF_2CF_2C(O)CF(CF_3)CF_2CF_3$ may be prepared by reacting $CBrF_2CF_2C(O)F$ with $CF_3CF=CFCF_3$; and $CF_3CBrFCF_2C(O)CF(CF_3)_2$ may be prepared by reacting $CF_3CBrFCF_2C(O)F$ with $CF_3CF=CF_2$.

The new monobromoperfluoroketones $CF_3C(O)CBr(CF_3)_2$, $CF_3CBrFC(O)CF_2CF_2CF_3$, $CF_3C(O)CBr(CF_3)CF_2CF_3$, $CF_3C(O)CF(CF_3)CBrFCF_3$, $CF_3CF_2CF_2C(O)CBr(CF_3)_2$, useful in the method of the present invention, may be prepared by reacting a perfluoroacyl fluoride with a monobromoperfluoroolefin.

$CF_3C(O)CBr(CF_3)_2$ may be prepared by reacting $CF_3C(O)F$ with $CF_3CBr=CF_2$; $CF_3CBrFC(O)CF_2CF_2CF_3$ may be prepared by reacting $CBrF=CF_2$ with $CF_3CF_2CF_2C(O)F$; a mixture of $CF_3C(O)CBr(CF_3)CF_2CF_3$ and $CF_3C(O)CF(CF_3)CBrFCF_3$ may be prepared by reacting $CF_3CBr=CFCF_3$ with $CF_3C(O)F$; and $CF_3CF_2CF_2C(O)CBr(CF_3)_2$ may be prepared by reacting $CF_3CF_2CF_2C(O)F$ with $CF_3CBr=CF_2$.

(Perfluoroalkoxy)monobromoperfluoroketones useful in the process of the present invention are of the formula $R^1C(O)CF(CF_3)OR^F$, wherein $R^1$ is a $C_1$ to $C_3$ monobromoperfluoroalkyl radical, and $R^F$ is a $C_1$ to $C_3$ perfluoroalkyl radical, may be obtained by reacting monobromoperfluoroacyl fluorides of the formula $R^1C(O)F$ with perfluorovinyl ethers of the formula $CF_2=CFOR^F$. Representative new (perfluoroalkoxy)monobromoperfluoroketones useful in the process of the present invention include $CBrF_2C(O)CF(CF_3)OCF_3$, $CBrF_2CF_2C(O)CF(CF_3)OCF_3$, $CBrF_2CF_2CF_2C(O)CF(CF_3)OCF_3$, $CBrF_2C(O)CF(CF_3)OC_2F_5$, $CBrF_2CF_2C(O)CF(CF_3)OC_2F_5$, $CBrF_2C(O)CF(CF_3)OCF_2C_2F_5$, $CBrF_2CF_2C(O)CF(CF_3)OCF_2C_2F_5$, $CBrF_2C(O)CF(CF_3)OCF(CF_3)_2$, $CBrF_2CF_2C(O)CF(CF_3)OCF(CF_3)_2$, $CF_3CBrFC(O)CF(CF_3)OCF(CF_3)_2$, $CF_3CBrFC(O)CF(CF_3)OCF_3$, and $CF_3CBrFC(O)CF(CF_3)OC_2F_5$.

$CBrF_2C(O)CF(CF_3)OCF_3$ may be prepared by reacting $CBrF_2C(O)F$ with $CF_2=CFOCF_3$; $CBrF_2CF_2C(O)CF(CF_3)OCF_3$ may be prepared by reacting $CBrF_2CF_2C(O)F$ with $CF_2=CFOCF_3$; $CBrF_2CF_2CF_2C(O)CF(CF_3)OCF_3$ may be prepared by reacting $CBrF_2CF_2CF_2C(O)F$ with $CF_2=CFOCF_3$; $CBrF_2C(O)CF(CF_3)OC_2F_5$ may be prepared by reacting $CBrF_2C(O)F$ with $CF_2=CFOC_2F_5$; $CBrF_2CF_2C(O)CF(CF_3)OC_2F_5$ may be prepared by reacting $CBrF_2CF_2C(O)F$ with $CF_2=CFOC_2F_5$; $CBrF_2C(O)CF(CF_3)OCF_2C_2F_5$ may be prepared by reacting $CBrF_2C(O)F$ with $CF_2=CFOCF_2C_2F_5$; $CBrF_2CF_2C(O)CF(CF_3)OCF_2C_2F_5$ may be prepared by reacting $CBrF_2CF_2C(O)F$ with $CF_2=CFOCF_2C_2F_5$; $CBrF_2C(O)CF(CF_3)OCF(CF_3)_2$ may be prepared by reacting $CBrF_2C(O)F$ with $CF_2=CFOCF(CF_3)_2$; $CBrF_2CF_2C(O)CF(CF_3)OCF(CF_3)_2$ may be prepared by reacting $CBrF_2CF_2C(O)F$ with $CF_2=CFO CF(CF_3)_2$; $CF_3CBrFC(O)CF(CF_3)OCF_3$ may be prepared by reacting $CF_3CBrFC(O)F$ with $CF_2=CFOCF_3$; and $CF_3CBrFC(O)CF(CF_3)OC_2F_5$ may be prepared by reacting $CF_3CBrFC(O)F$ with $CF_2=CFOC_2F_5$.

(Perfluoroalkoxy)monobromoperfluoroketones of the formula $R^1C(O)CF(CF_3)OR^F$ may also be obtained by reacting perfluoroalkoxyperfluoroacyl fluorides of the formula $R^FOCF(CF_3)C(O)F$ with a monobromoperfluoroolefin. Representative (perfluoroalkoxy)monobromoperfluoroketones useful in the process of the present invention include $CF_3CBrFC(O)CF(CF_3)OCF_3$, $(CF_3)_2CBrC(O)CF(CF_3)OCF_3$, $CF_3CBrFC(O)CF(CF_3)OC_2F_5$, $(CF_3)_2CBrC(O)CF(CF_3)OC_2F_5$, $CF_3CBrFC(O)CF(CF_3)OCF_2C_2F_5$, and $CF_3CBrFC(O)CF(CF_3)OCF(CF_3)_2$.

$CF_3CBrFC(O)CF(CF_3)OCF_3$ may be prepared by reacting $CF_3OC(CF_3)FC(O)F$ with $CF_2=CBrF$; $(CF_3)_2CBrC(O)CF(CF_3)OCF_3$ may be prepared by reacting $CF_3OC(CF_3)FC(O)F$ with $CF_3CBr=CF_2$; $CF_3CBrFC(O)CF(CF_3)OC_2F_5$ may be prepared by reacting $C_2F_5OC(CF_3)FC(O)F$ with $CF_2=CBrF$; $(CF_3)_2CBrC(O)CF(CF_3)OC_2F_5$ may be prepared by reacting $C_2F_5OC(CF_3)FC(O)F$ with $CF_3CBr=CF_2$; $CF_3CBrFC(O)CF(CF_3)OCF_2C_2F_5$ may be prepared by reacting $C_2F_5CF_2OC(CF_3)FC(O)F$ with $CF_2=CBrF$; and $CF_3CBrFC(O)CF(CF_3)OCF(CF_3)_2$ may be prepared by reacting $(CF_3)_2CFOC(CF_3)FC(O)F$ with $CF_2=CBrF$.

(Fluoroalkoxy)monobromoperfluoroketones useful in the process of the present invention are of the formula $R^1C(O)CX(CF_3)OR^2$, wherein X is H or F, $R^1$ is a $C_1$, $C_2$, or $C_3$ bromoperfluoroalkyl radical, and $R^2$ is a $C_1$ to $C_3$ alkyl or fluoroalkyl radical, may be prepared by reacting monobromoperfluoroacyl fluorides of the formula $R^1C(O)F$ with hydrofluorovinyl ethers of the formula $CF_2=CXOR^2$. Representative new (fluoroalkoxy)monobromoperfluoroketones include $CBrF_2C(O)CF(OCF_2CHF_2)CF_3$, $CBrF_2C(O)CH(OCF_2CHF_2)CF_3$, $CBrF_2C(O)CF(OCH_3)CF_3$, and $CBrF_2C(O)CF(CF_2OCH_3)CF_3$.

$CBrF_2C(O)CF(OCF_2CHF_2)CF_3$ may be prepared by reacting $CBrF_2C(O)F$ with $CF_2=CFOCF_2CHF_2$; $CBrF_2C(O)CH(OCF_2CHF_2)CF_3$ may be prepared by reacting $CBrF_2C(O)F$ with $CF_2=CHOCF_2CHF_2$; and $CBrF_2C(O)CF(OCH_3)CF_3$ may be prepared by reacting $CBrF_2C(O)F$ with $CF_2=CFOCH_3$.

Another (fluoroalkoxy)monobromoperfluoroketone useful in the process of the present invention includes $CBrF_2C(O)CF(CF_2OCH_3)CF_3$, prepared by reacting $CBrF_2C(O)F$ with $CF_3CF=CFOCH_3$.

The reaction of fluoroacyl fluorides with fluoroolefins is described by Fawcett, et al. in U. S. Pat. No. 3,185,734 and *Journal of the American Chemical Society*, Vol. 84, pages 4285 to 4288 (1962). The teachings of these references may be applied to the aforementioned preparation of monobromoperfluoroketones by the reaction of monobromoperfluoroacyl fluorides with perfluoroolefins as well as the aforementioned preparation of monobromoperfluoroketones by the reaction of perfluoroacyl fluorides with monobromoperfluoroolefins. The teachings of these references may also be applied to the preparation of (perfluoroalkoxy)monobromoperfluoroketones by the reaction of monobromoperfluoroacyl fluorides with perfluorovinyl ethers or by the reaction of perfluoroalkoxyperfluoroacyl fluorides with monobromoolefins. The teachings of these references may also be applied to the preparation of (fluoroalkoxy)monobromoperfluoroketones by the reaction of monobromoperfluoroacyl fluorides with hydrofluorovinyl ethers.

Though not essential for preparing the ketones of the present invention, reaction of a fluoroacyl fluoride (such as a perfluoroacyl fluoride or monobromoperfluoroacyl fluoride) with a fluoroolefin (such as a perfluoroolefin, monobromoperfluoroolefin, perfluorovinyl ether or hydrofluorovinyl ether) may be performed in a polar non-protic solvent such as N,N-dimethyl formamide, N,N-dimethyl acetamide, dimethyl sulfolane, dimethylsulfoxide, N-methylpyrrolidinone, and glycol ethers such as ethylene glycol dimethyl ether, diethylene glycol dimethyl ether, triethylene glycol dimethyl ether, and tetraethylene glycol dimethyl ether. Preferred solvents for reacting fluoroacyl fluorides with fluoroolefin are glycol ethers. The reaction may be run under substantially anhydrous conditions.

The mole ratio of the fluoroolefin to fluoroacyl fluoride during the reaction may be at least about 1:1 to about 2:1, and preferably is about 1.1. More than about 2 moles of fluoroolefin per mole of fluoroacyl fluoride provides little benefit.

The reaction of fluoroacyl fluoride with fluoroolefin is preferably conducted in the presence of a fluoride ion source such as an alkali metal fluoride, alkali metal hydrogen difluoride (i.e., a bifluoride), alkali-earth metal fluoride, tetraalkylammonium fluoride, tetraalkylammonium hydrogen fluoride, trialkylammonium fluoride, or non-oxidizing transition metal fluorides. Preferred fluoride ion sources are potassium fluoride, cesium fluoride, and potassium bifluoride. The fluoride ion source may be present at a level of 5 mole percent to 20 mole percent, preferably about 10 mole percent, based on the quantity of fluoroolefin present.

Temperatures of from about 50° C. to about 250° C., preferably from about 100° C. to about 150° C. are effective to produce any of the fluorinated ketones of the present invention by reaction of a fluoroacyl fluoride with a fluoroolefin.

The reaction of fluoroacyl fluoride with fluoroolefin may take place in batch mode or in semi-batch mode with the fluoroacyl fluoride added gradually to the mixture of the fluoroolefin, solvent, and fluoride ion source. Contact times suitable for the reaction may be from about 0.5 hour to about 24 hours. The reaction typically takes place under autogenous pressure provided by the reactants at the reaction temperature.

Though not added intentionally to the reactions, hydrogen fluoride may be present in small amounts during the reactions of fluoroacyl fluorides due to the presence of traces of water. Reaction of fluoroacyl fluorides with fluoroolefins may be conducted in a vessel formed of materials compatible with hydrogen fluoride at elevated temperatures and pressures. Examples of such materials include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The fluoroketone products may be isolated from the reaction mixture as a lower liquid layer or by distillation. After removing traces of fluoride salts by washing with water, such products may be purified by distillation.

The method of the present invention further includes use of monohydromonobromoperfluoroketones in which one of the C—F bonds in a perfluoroketone has been replaced by a C—Br bond, and in addition, another of the C—F bonds in said perfluoroketone has been replaced by a C—H bond. New monohydromonobromoperfluoroketones useful in the process of the present invention comprise $CHF_2CF_2C(O)CBrFCF_3$, $(CF_3)_2CHC(O)CBrFCF_3$, $CHF_2CF_2C(O)CBr(CF_3)_2$, $(CF_3)_2CHC(O)CBr(CF_3)_2$, $(CF_3)_2CHC(O)CBrF_2$, and $CBrF_2CF_2C(O)CH(CF_3)_2$.

$CHF_2CF_2C(O)CBrFCF_3$ may be prepared by reacting $CHF_2CF_2C(O)F$ with $CBrF=CF_2$; $(CF_3)_2CHC(O)CBrFCF_3$ may be prepared by reacting $(CF_3)_2CHC(O)F$ with $CBrF=CF_2$; $CHF_2CF_2C(O)CBr(CF_3)_2$ may be prepared by reacting $CHF_2CF_2C(O)F$ with $CF_3CBr=CF_2$; $(CF_3)_2CHC(O)CBr(CF_3)_2$ may be prepared by reacting $(CF_3)_2CHC(O)F$ with $CF_3CBr=CF_2$; and $CBrF_2CF_2C(O)CH(CF_3)_2$ may be prepared by reacting $CBrF_2CF_2C(O)F$ with $CF_3CH=CF_2$. The monohydromonobromoperfluoroketone $(CF_3)_2CHC(O)CBrF_2$ may be prepared by the reaction of the bromofluoroacyl fluoride $CBrF_2C(O)F$ with the monohydroperfluoroolefin $CF_3CH=CF_2$.

The production of monohydromonobromoperfluoroketones by the reaction of monohydroperfluoroacyl fluorides with monobromoperfluoroolefins, as well as by the reaction of monobromoperfluoroacyl fluorides with monohydroperfluoroolefins, may use reaction conditions and procedure similar to those discussed hereinabove for the reaction of a fluoroacyl fluoride with a fluoroolefin.

The method of the present invention further includes use of monochloromonobromoperfluoroketones in which one of the C—F bonds in a perfluoroketone has been replaced by a C—Br bond, and in addition, another one of the C—F bonds in said perfluoroketone has been replaced by a C—Cl bond. Monochloromonobromoperfluoroketones useful in the process of the present invention comprise compounds of the formula $CXF_2CFYC(O)CFRCF_3$, wherein X is Cl and Y is Br, or wherein X is Br and Y is Cl, and wherein R is F, a $CF_3$ radical, or a $C_2F_5$ radical. These compounds may be prepared by contacting an acid fluoride of the formula $CXF_2CFYC(O)F$, prepared as disclosed by Darst, et al. in U.S. Pat. No. 5,557,010, with a perfluoroolefin of the formula $CFR=CFR$.

Representative monochloromonobromoperfluoroketones include $CClF_2CFBrC(O)CF_2CF_3$, prepared by reacting $CClF_2CFBrC(O)F$ with $CF_2=CF_2$; $CBrF_2CClFC(O)CF_2CF_3$, prepared by reacting $CBrF_2CClFC(O)F$ with $CF_2=CF_2$; $CClF_2CFBrC(O)CF(CF_3)_2$, prepared by reacting $CClF_2CFBrC(O)F$ with $CF_2=CFCF_3$; and $CBrF_2CClFC(O)CF(CF_3)_2$, prepared by reacting $CBrF_2CClFC(O)F$ with $CF_2=CFCF_3$.

Monochloromonobromoperfluoroketones useful in the method of the present invention further comprise $CClF_2C(O)CBr(CF_3)_2$, $CClF_2CF_2C(O)CBr(CF_3)_2$, $CF_3CClFC(O)CBr(CF_3)_2$, $CClF_2C(O)CBrFCF_3$, $CClF_2CF_2C(O)CBrFCF_3$, and $CF_3CClFC(O)CBrFCF_3$ which may be prepared by reacting a monochloroperfluoroacyl fluoride with a monobromoperfluoroolefin.

$CClF_2C(O)CBr(CF_3)_2$ may be prepared by reacting $CClF_2C(O)F$ with $CF_3CBr=CF_2$; $CClF_2CF_2C(O)CBr(CF_3)_2$ may be prepared by reacting $CClF_2CF_2C(O)F$ with $CF_3CBr=CF_2$; $CF_3CClFC(O)CBr(CF_3)_2$ may be prepared by reacting $CF_3CClFC(O)F$ with $CF_3CBr=CF_2$; $CClF_2C(O)CBrFCF_3$ may be prepared by reacting $CClF_2C(O)F$ with $CF_2=CBrF$; $CClF_2CF_2C(O)CBrFCF_3$ may be prepared by reacting CClF$_2$CF$_2$(O)F with CF$_2$=CBrF; CF$_3$CClFC(O)CBrFCF$_3$ may be prepared by reacting CF$_3$CClFC(O)F with CF$_2$=CBrF.

Monochloromonobromoperfluoroketones useful in the method of the present invention further include CBrF$_2$C(O)CCl(CF$_3$)$_2$, CBrF$_2$CF$_2$C(O)CCl(CF$_3$)$_2$, CBrF$_2$C(O)CClFCF$_3$, and CBrF$_2$CF$_2$C(O)CClFCF$_3$ which may be prepared by reacting a monobromoperfluoroacyl fluoride with a monochloroperfluoroolefin.

CBrF$_2$C(O)CCl(CF$_3$)$_2$ may be prepared by reacting CBrF$_2$C(O)F with CF$_3$CCl=CF$_2$; CBrF$_2$CF$_2$C(O)CCl(CF$_3$)$_2$ may be prepared by reacting CBrF$_2$CF$_2$C(O)F with CF$_3$CCl=CF$_2$; CBrF$_2$C(O)CClFCF$_3$ may be prepared by reacting CBrF$_2$C(O)F with CF$_2$=CClF; and CBrF$_2$CF$_2$C(O)CClFCF$_3$ may be prepared by reacting CBrF$_2$CF$_2$C(O)F with CF$_2$=CClF.

The formation of monohydromonobromoperfluoroketones by the reaction of fluoroacyl fluorides of the formula CXF$_2$CFYC(O)F with perfluoroolefins, or by the reaction of monochloroperfluoroacyl fluorides with monobromoperfluoroolefins, or by the reaction of monobromoperfluoroacyl fluorides with monochloroperfluoroolefins, may use reaction conditions and procedure similar to those discussed hereinabove for the reaction of a fluoroacyl fluoride with a fluoroolefin.

EXAMPLES

Example 1

Syntheses of CF$_3$CBrFC(O)C$_2$F$_5$ and CF$_3$C(O)CBrFC$_2$F$_5$

Preparation of Perfluoro2,3-epoxypentane

A 2 L creased flask was equipped with a mechanical stirrer, a thermocouple well, an addition funnel, and a dry ice distillation head connected to a calcium sulfate drying tube. The flask was charged with 800 mL of sodium hypochlorite solution (10-13% chlorine) and 15.0 g of tetrabutylammonium hydrogen sulfate. The addition funnel was charged with 60.0 g (0.24 mole) of cold perfluoro-2-pentene. The solution was cooled to 20° C. using an ice-water bath and the mixture stirred at 600 rpm. The F-2-pentene was then added to the sodium hypochlorite solution over the course of about one hour while maintaining the temperature of the reaction in the range of 20-22° C. After the addition was complete, the mixture was stirred for an additional hour. The flask was then set for distillation and the epoxide product (32.8 g, CAS Reg. No. [71917-15-2]) was then distilled out of the mixture by raising the pot temperature to about 40° C.

Preparation of a Mixture of Perfluoro-2-bromo-3-Pentanone and Perfluoro-3-bromo-2-pentanone A one liter flask was equipped with a mechanical stirrer, a thermocouple well, and a dry ice condenser connected to a Drierite™ tube. The flask was charged with 146.3 g (1.42 moles) of sodium bromide, 10 g (0.031 mole) of tetrabutyl ammonium bromide, and 235.8 g (300 mL) of acetonitrile. The mixture was stirred for 15 minutes at room temperature and then cooled to about 6° C. using an ice-water bath. A 32.9 g (0.12 mole) sample of perfluoro2,3-epoxypentane, prepared as described above, was then added to the flask in one portion. The ice bath was removed and the reaction was stirred rapidly for six hours at room temperature.

The flask was then set for vacuum distillation. The bromo-perfluoropentanone mixture (50.3 g) was then distilled out of the flask at a pressure of about 80 mm Hg and a pot temperature about 20-25° C. Analysis of the distillate by gas chromography-mass spectroscopy indicated it was primarily an azeotropic mixture of acetonitrile (31.1 GC area %), perfluoro-2-bromo-3-pentanone (13.6%), and perfluoro-3-bromo-2-pentanone (47.0%).

The distillate was subjected to flash chromatography on silica gel using octane as an eluant. The column effluent containing primarily octane and the mixture of perfluoro-2-bromo-3-pentanone and perfluoro-3-bromo-2-pentanone was then subjected to two vacuum distillations at a pressure of 56 and 100 torr, respectively, to separate the bromoperfluoroketones from the bulk of the octane. The low-boiling fractions from the vacuum distillations were then re-distilled at atmospheric pressure. The fractions collected at a head temperature of 71.2-72.8° C. were combined. The product was a mixture of perfluoro-2-bromo-3-pentanone and perfluoro-3-bromo-2-pentanone in molar ratio of 1.0 to 1.12 with overall purity of >98 GC area %.

Example 2

Fire Extinguishing Concentration of a Mixture of CF$_3$CBrFC(O)C$_2$F$_5$ and CF$_3$C(O)CBrFC$_2$F$_5$ The fire extinguishing concentration of a mixture of CF$_3$CBrFC(O)C$_2$F$_5$ and F$_3$C(O)CBrFC$_2$F$_5$, in a 1.0 to 1.12 mole ratio respectively, was determined by the ICI Cup Burner method. This method is described in "Measurement of Flame-Extinguishing Concentrations" R. Hirst and K. Booth, Fire Technology, vol. 13(4): 296-315 (1977).

Specifically, an air stream is passed at 40 liters/minute through an outer chimney (8.5 cm. I. D. by 53 cm. tall) from a glass bead distributor at its base. A fuel cup burner (3.1 cm. O.D. and 2.15 cm. I.D.) is positioned within the chimney at 30.5 cm. below the top edge of the chimney. The fire extinguishing agent is added to the air stream prior to its entry into the glass bead distributor while the air flow rate is maintained at 40 liters/minute for all tests. The air and agent flow rates are measured using calibrated rotameters.

The test is conducted by adjusting the fuel (n-heptane) level in the reservoir to bring the liquid fuel level in the cup burner just even with the ground glass lip on the burner cup. With the air flow rate maintained at 40 liters/minute, the fuel in the cup burner is ignited. The fire extinguishing agent is added in measured increments until the flame is extinguished.

The fire extinguishing concentration is determined from the following equation: Extinguishing concentration=$(F_1/(F_1+F_2))\times 100$, where $F_1$ is the agent flow rate and $F_2$ is the air flow rate.

TABLE 1

| FIRE EXTINGUISHING AGENT | FIRE EXTINGUISHING CONCENTRATION (volume % in air) |
|---|---|
| EXAMPLE | |
| CF$_3$CBrFC(O)C$_2$F$_5$ and F$_3$C(O)CBrFC$_2$F$_5$ in a 1.0 to 1.12 mole ratio mixture, respectively | 3.5 |
| COMPARATIVE | |
| CF$_3$CHFCF$_3$ (HFC-227ea) | 7.3 |
| CF$_3$CHFCHF$_2$ (HFC-236ea) | 10.2 |
| CF$_3$CF$_2$CH$_2$Cl (HCFC-235cb) | 6.2 |
| CF$_4$ | 20.5 |
| C$_2$F$_6$ | 8.7 |

TABLE 1-continued

| FIRE EXTINGUISHING AGENT | FIRE EXTINGUISHING CONCENTRATION (volume % in air) |
|---|---|
| $CF_3Br$ (Halon-1301) | 4.2 |
| $CF_2ClBr$ (Halon 1211) | 6.2 |
| $CHF_2Cl$ | 13.6 |

What is claimed is:

1. A method of extinguishing a fire comprising applying to said fire a composition at least one compound selected from the group consisting of (perfluoroalkoxy)monobromoperfluoroketones and (fluoroalkoxy)monobromoperfluoroketones in an amount sufficient to extinguish said fire.

2. The method of claim 1 wherein said composition comprises a (perfluoroalkoxy)monobromoperfluoroketones.

3. The method of claim 2 wherein said (perfluoroalkoxy)monobromoperfluoroketones is selected from the compounds having the formula $R^1C(O)CF(CF_3)OR^F$, wherein $R^1$ is a $C_1$ to $C_3$ monobromoperfluoroalkyl radical, and Rf is a C1 to C3 perfluoroalkyly radical.

4. The method of claim 3 wherein said (perfluoroalkoxy)monobromoperfluoroketones is selected from the group consisting of: $CBrF_2C(O)CF(CF_3)OCF_3$, $CBrF_2CF_2C(O)CF(CF_3)OCF_3$, $CBrF_2CF_2CF_2C(O)CF(CF_3)OCF_3$, $CBrF_2C(O)CF(CF_3)OC_2F_5$, $CBrF_2CF_2C(O)CF(CF_3)OC_2F_5$, $CBrF_2C(O)CF(CF_3)OCF_2C_2F_5$, $CBrF_2CF_2C(O)CF(CF_3)OCF_2C_2F_5$, $CBrF_2C(O)CF(CF_3)OCF(CF_3)_2$, $CBrF_2CF_2C(O)CF(CF_3)OCF(CF_3)_2$, $CF_3CBrFC(O)CF(CF_3)OCF(CF_3)_2$, $CF_3CBrFC(O)CF(CF_3)OCF_3$, $(CF_3)_2CBrC(O)CF(CF_3)OCF_3$, $CF_3CBrFC(O)CF(CF_3)OC_2F_5$, $(CF_3)_2CBrC(O)CF(CF_3)OC_2F_5$, $CF_3CBrFC(O)CF(CF_3)OCF_2C_2F_5$, and $CF_3CBrFC(O)CF(CF_3)OCF(CF_3)_2$.

5. The method of claim 1 wherein said composition comprises a (fluoroalkoxy)monobromoperfluoroketones.

6. The method of claim 5 wherein said (fluoroalkoxy)monobromoperfluoroketone is selected from compounds having the formula $R^1C(O)CX(CF_3)OR^2$, wherein X is H or F, $R^1$ is a $C_1$, $C_2$ or $C_3$ bromoperfluoroalkyl radical, and $R^2$ is a $C_1$ to $C_3$ alkyl or fluoroalkyl radical.

7. The method of claim 6 wherein said (fluoroalkoxy)monobromoperfluoroketone is selected from the group consisting of: CBrF2C(O)CF(OCF2CHF2)CF3, CBrF2C(O)CH(OCF2CHF2)CF3, CBrF2C(O)CF(OCF2CHF2)CF3, CBrF2C(O)CH(OCF2CHF2)CF3, CBrF2C(O)CF(OCH3)CF3, and CBrF2C(O)CF(CF2OCH3)CF3.

8. A method of preventing fire in an air-containing enclosed area containing combustible materials comprising introducing into said area a composition comprising at least one compound selected from the group consisting of (perfluoroalkoxy)monobromoperfluoroketones and (fluoroalkoxy)monobromoperfluoroketones, and maintaining said composition in an amount sufficient to suppress combustion of combustible materials in the enclosed area.

9. The method of claim 8 wherein said composition comprises a (perfluoroalkoxy)monobromoperfluoroketone.

10. The method of claim 9 wherein said (perfluoroalkoxy)monobromoperfluoroketone is selected from the compounds having the formula $R^1C(O)CF(CF_3)OR^F$, wherein $R^1$ is a $C_1$ to $C_3$ monobromoperfluoroalkyl radical, and $R^F$ is a $C_1$ to $C_3$ perfluoroalkyl radical.

11. The method of claim 10 wherein said (perfluoroalkoxy)monobromoperfluoroketone is selected from the group consisting of: $CBrF_2C(O)CF(CF_3)OCF_3$, $CBrF_2CF_2C(O)CF(CF_3)OCF_3$, $CBrF_2CF_2CF_2C(O)CF(CF_3)OCF_3$, $CBrF_2C(O)CF(CF_3)OC_2F_5$, $CBrF_2CF_2C(O)CF(CF_3)OC_2F_5$, $CBrF_2C(O)CF(CF_3)OCF_2C_2F_5$, $CBrF_2CF_2C(O)CF(CF_3)OCF_2C_2F_5$, $CBrF_2C(O)CF(CF_3)OCF(CF_3)_2$, $CBrF_2CF_2C(O)CF(CF_3)OCF(CF_3)_2$, $CF_3CBrFC(O)CF(CF_3)OCF(CF_3)_2$, $CF_3CBrFC(O)CF(CF_3)OCF_3$, $(CF_3)_2CBrC(O)CF(CF_3)OCF_3$, $CF_3CBrFC(O)CF(CF_3)OC_2F_5$, $(CF_3)_2CBrC(O)CF(CF_3)OC_2F_5$, $CF_3CBrFC(O)CF(CF_3)OCF_2C_2F_5$, and $CF_3CBrFC(O)CF(CF_3)OCF(CF_3)_2$.

12. The method of claim 8 wherein said composition comprises a (fluoroalkoxy)monobromoperfluoroketone.

13. The method of claim 12 wherein said (fluoroalkoxy)monobromoperfluoroketone is selected from compounds having the formula $R^1C(O)CX(CF_3)OR^2$, wherein X is H or F, $R^1$ is a $C_1$, $C_2$ or $C_3$ bromoperfluoroalkyl radical, and $R^2$ is a $C_1$ to $C_3$ alkyl or fluoroalkyl radical.

14. The method of claim 13 wherein said (fluoroalkoxy)monobromoperfluoroketone is selected from the group consisting of: $CBrF_2C(O)CF(OCF_2CHF_2)CF_3$, $CBrF_2C(O)CH(OCF_2CHF_2)CF_3$, $CBrF_2C(O)CF(OCH_3)CF_3$, and $CBrF_2C(O)CF(CF_2OCH_3)CF_3$.

* * * * *